(12) United States Patent
Yoshida

(10) Patent No.: US 10,667,698 B2
(45) Date of Patent: Jun. 2, 2020

(54) METHODS FOR ESTIMATING POST-PCI FRACTIONAL FLOW RESERVE

(71) Applicant: Masayoshi Yoshida, Ottawa (CA)

(72) Inventor: Masayoshi Yoshida, Ottawa (CA)

(*) Notice: Subject to any disclaimer, the term of this patent is extended or adjusted under 35 U.S.C. 154(b) by 414 days.

(21) Appl. No.: 15/587,523

(22) Filed: May 5, 2017

(65) Prior Publication Data

US 2017/0325696 A1    Nov. 16, 2017

Related U.S. Application Data

(60) Provisional application No. 62/335,418, filed on May 12, 2016.

(51) Int. Cl.

| | |
|---|---|
| A61B 8/06 | (2006.01) |
| A61B 5/02 | (2006.01) |
| A61B 5/026 | (2006.01) |
| A61B 5/0215 | (2006.01) |
| A61B 5/00 | (2006.01) |
| A61B 5/06 | (2006.01) |
| A61B 8/04 | (2006.01) |
| A61B 8/08 | (2006.01) |
| A61B 6/12 | (2006.01) |

(52) U.S. Cl.
CPC ........ *A61B 5/02007* (2013.01); *A61B 5/0215* (2013.01); *A61B 5/0261* (2013.01); *A61B 5/02154* (2013.01); *A61B 5/066* (2013.01); *A61B 5/4848* (2013.01); *A61B 5/6851* (2013.01); *A61B 5/7278* (2013.01); *A61B 6/12* (2013.01); *A61B 8/04* (2013.01); *A61B 8/06* (2013.01); *A61B 8/0891* (2013.01); *A61B 8/5223* (2013.01)

(58) Field of Classification Search
CPC ............................ G01N 21/85; G01B 9/02091
USPC .................................................. 600/561, 342
See application file for complete search history.

(56) References Cited

U.S. PATENT DOCUMENTS

8,317,715 B2 * 11/2012 Belleville ............ A61B 5/0215
600/485
8,609,066 B2 * 12/2013 Rosenmeier ....... A61K 51/0476
424/9.1

(Continued)

OTHER PUBLICATIONS

Measurement of Fractional Flow Reserve to Assess the Functional Severity of Coronary-Artery Stenoses Nico H.J. Pijls, M.D., Ph.D., Bernard de Bruyne, M.D., Kathinka Peels, M.D., 1996.*

*Primary Examiner* — Suzette J Gherbi
(74) *Attorney, Agent, or Firm* — Kubotera & Associates, LLC

(57) ABSTRACT

Methods for diagnosing and/or treating a multi-lesion intravascular region are disclosed. The methods may include advancing a pressure sensing device to a first position that is distal of a first lesion and that is distal of a second lesion, proximally retracting the pressure sensing device to a second position that is proximal of the first lesion and that is proximal of the second lesion, calculating a first estimated post-treatment fractional flow reserve based on treatment of the first lesion, calculating a second estimated post-treatment fractional flow reserve based on treatment of the second lesion, and treating the first lesion, the second lesion, or both based on the first estimated post-treatment fractional flow reserve and the second estimated post-treatment fractional flow reserve.

9 Claims, 12 Drawing Sheets

(56) References Cited

U.S. PATENT DOCUMENTS

| | | | | |
|---|---|---|---|---|
| 8,641,639 | B2* | 2/2014 | Manstrom | A61M 5/007 600/561 |
| 8,700,130 | B2* | 4/2014 | Iddan | A61B 6/5217 600/424 |
| 9,775,567 | B2* | 10/2017 | Suchecki | A61B 5/02007 |
| 2010/0241008 | A1* | 9/2010 | Belleville | A61B 5/0215 600/478 |
| 2014/0257087 | A1* | 9/2014 | Elbasiony | A61B 5/061 600/424 |
| 2014/0276139 | A1* | 9/2014 | Burkett | A61B 5/02156 600/486 |
| 2014/0276191 | A1* | 9/2014 | Kassab | A61B 5/02007 600/547 |
| 2014/0276687 | A1* | 9/2014 | Goodman | A61B 18/24 606/10 |
| 2014/0379269 | A1* | 12/2014 | Schmitt | A61B 5/6852 702/19 |
| 2015/0141854 | A1* | 5/2015 | Eberle | A61B 5/02154 600/488 |
| 2015/0359445 | A1* | 12/2015 | Ehr | A61B 5/02007 600/487 |
| 2016/0106373 | A1* | 4/2016 | Suchecki | A61B 5/02007 600/486 |
| 2017/0360376 | A1* | 12/2017 | Suchecki | A61B 5/02007 |

* cited by examiner

METHODS FOR ESTIMATING POST-PCI FRACTIONAL FLOW RESERVE

TECHNICAL FIELD

The present disclosure pertains to medical devices and methods for using medical devices. More particularly, the present disclosure pertains to methods for estimating fractional flow reserve.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for using medical devices.

SUMMARY

This disclosure provides design, material, manufacturing method, and use alternatives for medical devices. In one example, a method for diagnosing and/or treating a multi-lesion intravascular region is disclosed. The method comprises:

advancing a pressure sensing device to a first position that is distal of a first lesion and that is distal of a second lesion and distal of vessel;

proximally retracting the pressure sensing device to a second position that is distal of the first lesion and that is distal of the second lesion and at the position of distal edge of treatment of first lesion;

proximally retracting the pressure sensing device to a third position that is proximal of the first lesion and that is distal of the second lesion and at the position of proximal edge of treatment of first lesion;

proximally retracting the pressure sensing device to a fourth position that is proximal of the first lesion and that is distal of the second lesion and at the position of distal edge of treatment of second lesion;

proximally retracting the pressure sensing device to a fifth position that is proximal of the first lesion and that is proximal of the second lesion and at the position of proximal edge of treatment of second lesion; proximally retracting the pressure sensing device to a sixth position that is proximal of the first lesion and that is proximal of the second lesion and at the ostium lesion of vessels;

calculating a first estimated post-treatment fractional flow reserve based on treatment of the first lesion;

calculating a second estimated post-treatment fractional flow reserve based on treatment of the second lesion; and treating the first lesion, the second lesion, or both based on the first estimated post-treatment fractional flow reserve and the second estimated post-treatment fractional flow reserve.

It can apply to third, forth, fifth, lesions.

Alternatively or additionally to any of the embodiments above, calculating a first estimated post-treatment fractional flow reserve based on treatment of the first lesion includes:

measuring an aortic pressure ($P_a$), measuring a distal pressure distal of the first lesion at the distal of vessel ($P_d$), measuring a distal pressure distal of the first lesion at the position of distal edge of treatment of first lesion ($P_{md}$), and measuring a proximal pressure distal of the first lesion at the position of proxymal edge of treatment of first lesion ($P_{mp}$); and wherein the first estimated fractional flow reserve is equal to:

$$P_d/(P_a-(P_{mp}-P_{md})).$$

Alternatively or additionally to any of the embodiments above, calculating a first estimated post-treatment fractional flow reserve based on treatment of the first lesion includes:

measuring an aortic pressure ($P_a$), measuring a distal pressure distal of the first lesion at the distal of vessel ($P_d$), measuring a pressure gradient ($P_g$) across the first lesion, and wherein the second estimated fractional flow reserve is equal to:

$$P_d/(P_a-(Pg)).$$

Alternatively or additionally to any of the embodiments above, further comprising calculating a third estimated post-treatment fractional flow reserve based on estimated post-treatment FFR of both the first lesion and the second lesion.

Alternatively or additionally to any of the embodiments above, calculating the third estimated post-treatment fractional flow reserve of first lesion includes:

determining a first fractional flow reserve ($FFR_1$) at the first position, and determining a second fractional flow reserve ($FFR_2$) at a second position that is distal of the first lesion; and determining a third fractional flow reserve ($FFR_3$) at a third position that is proxymal of the first lesion; and wherein the third estimated fractional flow reserve is equal to:

$$FFR_1/(1-(FFR_3-FFR_2)).$$

Alternatively or additionally to any of the embodiments above, calculating the third estimated post-treatment fractional flow reserve of first lesion includes:

determining a first fractional flow reserve ($FFR_1$) at the first position, and that is also at the position of distal edge of treatment of first lesion distal of the first lesion; and determining a third fractional flow reserve ($FFR_3$) at a third position that is proximal of the first lesion; and wherein the first estimated fractional flow reserve is equal to:

$$FFR_1/(1-(FFR_3-FFR_1)).$$

Alternatively or additionally to any of the embodiments above, further comprising proximally retracting the pressure sensing device to a fourth position that is proximal of a lesions and that is at the ostium portion of vessel (coronary artery) calculating a fourth estimated post-treatment fractional flow reserve based on treatment of the lesions.

Alternatively or additionally to any of the embodiments above, calculating the fourth estimated post-treatment fractional flow reserve includes:

determining a second fractional flow reserve ($FFR_2$) at the second position; and wherein the fourth estimated fractional flow reserve is equal to:

$$FFR_1/(1-(1-FFR_2)).$$

Alternatively or additionally to any of the embodiments above, further comprising co-registering the location of the pressure sensing device relative to the first lesion, the second lesion, or both with an imaging device.

Alternatively or additionally to any of the embodiments above, calculating a estimated post-treatment fractional flow reserve based on treatment of the first lesion is based on images from the imaging device.

Alternatively or additionally to any of the embodiments above, the imaging device includes an ultrasound imaging device.

Alternatively or additionally to any of the embodiments above, the imaging device includes an X-ray imaging device, an angiographic imaging device, an optical coherence tomography imaging device, or a computerized tomography imaging device.

Alternatively or additionally to any of the embodiments above, treating the first lesion, the second lesion, or both based on the first estimated post-treatment fractional flow reserve and the second estimated post-treatment fractional flow reserve includes the grade of collateral flow adjacent to the first lesion, the second lesion, or both.

A method for diagnosing and/or treating a medical condition is disclosed. The method comprises:
advancing a pressure sensing guidewire to a first position that is distal of a plurality of intravascular lesions, the pressure sensing guidewire comprising:
an elongate shaft having a distal housing region,
an optical pressure sensor disposed within the distal housing region, and
an optical fiber coupled to the pressure sensor and extending proximally therefrom;
proximally retracting the pressure sensing guidewire to a sixth position that is proximal of the plurality of intravascular lesions to gather fractional flow reserve data;
calculating one or more estimated fractional flow reserve values based on treatment of one or more of the plurality of intravascular lesions; and
treating one or more of the plurality of lesions based on the one or more estimated fractional flow reserve values.

Alternatively or additionally to any of the embodiments above, further comprising co-registering the location of the pressure sensing guidewire with an imaging device while proximally retracting the pressure sensing guidewire.

Alternatively or additionally to any of the embodiments above, the plurality of intravascular lesions includes a first lesion, a second lesion disposed proximal of the first lesion, and a third lesion disposed proximal of the second lesion; and
wherein calculating one or more estimated fractional flow reserve values includes calculating a first fractional flow reserve based on treating the first lesion and the second lesion.

Alternatively or additionally to any of the embodiments above, calculating one or more estimated fractional flow reserve values includes calculating a second fractional flow reserve based on treating the second lesion and the third lesion.

Alternatively or additionally to any of the embodiments above, treating one or more of the plurality of lesions includes treating the first lesion and the second lesion without treating the third lesion.

Alternatively or additionally to any of the embodiments above, treating one or more of the plurality of lesions includes treating the second lesion and the third lesion without treating the first lesion.

A method for diagnosing and/or treating a medical condition is disclosed. The method comprises:
advancing a pressure sensing guidewire to a first position that is distal of a plurality of intravascular lesions;
wherein the plurality of intravascular lesions includes a first lesion, a second lesion disposed proximal of the first lesion, and a third lesion disposed proximal of the second lesion;
proximally retracting the pressure sensing guidewire to a second position that is proximal of the third lesion;
co-registering the location of the pressure sensing guidewire with an imaging device while proximal retracting the pressure sensing guidewire;
calculating a first estimated fractional flow reserve based on placing one or more stents across the first lesion and the second lesion;
calculating a second estimated fractional flow reserve based on placing one or more stents across the second lesion and the third lesion;
treating the first lesion and the second lesion without treating the third lesion or treating the second lesion and the third lesion without treating the first lesion.

Alternatively or additionally to any of the embodiments above, the pressure sensing guidewire includes an optical pressure sensor.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
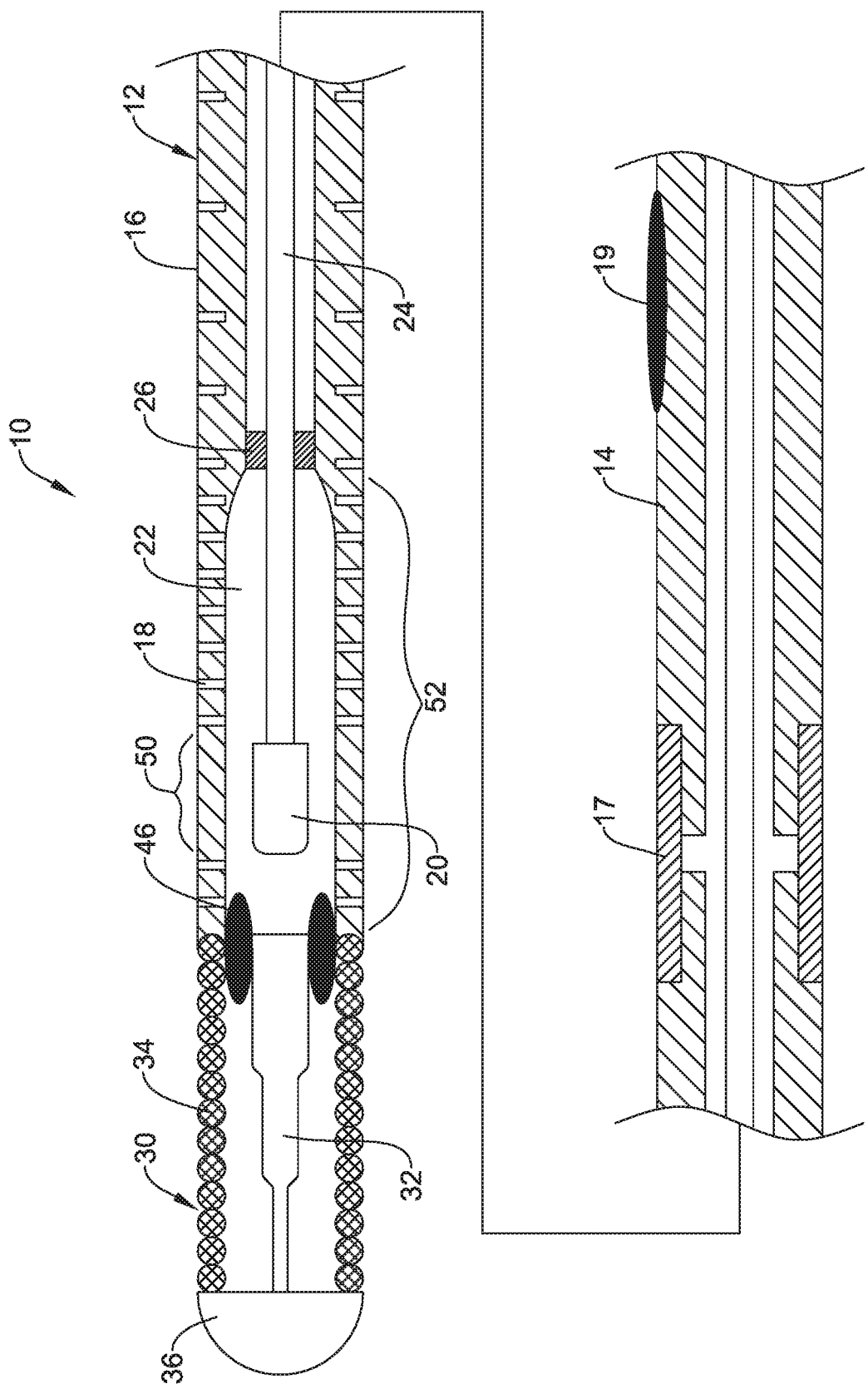
FIG. 1 is a partial cross-sectional side view of an example medical device.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

During some medical interventions, it may be desirable to measure and/or monitor the blood pressure within a blood vessel. For example, some medical devices may include pressure sensors that allow a clinician to monitor blood pressure. Such devices may be useful in determining fractional flow reserve (FFR), which may be understood as the ratio of the pressure after or distal of an intravascular lesion or stenosis (e.g., $P_d$) relative to the pressure before the lesion and/or the aortic pressure (e.g., $P_a$). In other words, FFR may be understood as $P_d/P_a$.

FIG. 1 illustrates a portion of an example medical device 10. In this example, medical device 10 is a blood pressure sensing guidewire 10. However, this is not intended to be limiting as other pressure sensing medical devices are contemplated including, for example, pressure sensing catheters, pressure sensing shafts, pressure sensing leads, pressure sensing wires, or the like. References to and/or discussion of a guidewire or pressure sensing guidewire herein may also apply to other pressure sensing medical devices, to the extent applicable, and should be interpreted as applying to such pressure sensing medical devices. Guidewire 10 may include a tubular member or shaft 12. Shaft 12 may include a proximal portion 14 and a distal portion 16. The materials for proximal portion 14 and distal portion 16 may vary and, in at least some instances, may include those materials disclosed herein. For example, proximal portion 14, distal portion 16, or both may include a nickel-cobalt-chromium-molybdenum alloy (e.g., MP35-N), a nickel-titanium alloy, stainless steel, or the like. These are just examples. Other materials may also be utilized.

In some embodiments, proximal portion 14 and distal portion 16 are formed from the same monolith of material. In other words, proximal portion 14 and distal portion 16 are portions of the same tube that defines shaft 12. In other embodiments, proximal portion 14 and distal portion 16 are separate tubular members that are joined together. For example, a section of the outer surface of portions 14/16 may be removed and a sleeve 17 may be disposed over the removed sections to join portions 14/16. Alternatively, sleeve 17 may be simply disposed over portions 14/16. Other bonds may also be used including welds, thermal bonds, adhesive bonds, or the like. If utilized, sleeve 17 used to join proximal portion 14 with distal portion 16 may include a material that desirably bonds with both proximal portion 14 and distal portion 16. For example, sleeve 17 may include a nickel-chromium-molybdenum alloy (e.g., INCONEL).

A plurality of slots 18 may be formed in shaft 12. In at least some embodiments, slots 18 are formed in distal portion 16. In some of these and in other instances, proximal portion 14 lacks slots 18. However, proximal portion 14 may include slots 18. Slots 18 may be desirable for a number of reasons. For example, slots 18 may provide a desirable level of flexibility to shaft 12 (e.g., along distal portion 16) while also allowing suitable transmission of torque. Slots 18 may be arranged/distributed along distal portion 16 in a suitable manner including any of those arrangements disclosed herein. For example, slots 18 may be arranged as opposing pairs of slots 18 that are distributed along the length of distal portion 16. In some embodiments, adjacent pairs of slots 18 may have a substantially constant spacing relative to one another. Alternatively, the spacing between adjacent pairs may vary. For example, more distal regions of distal portion 16 may have a decreased spacing (and/or increased slot density), which may provide increased flexibility. In other embodiments, more distal regions of distal portion 16 may have an increased spacing (and/or decreased slot density). These are just examples. Other arrangements are contemplated.

A pressure sensor 20 may be disposed within shaft 12 (e.g., within a lumen 22 of shaft 12). While pressure sensor 20 is shown schematically in FIG. 1, it can be appreciated that the structural form and/or type of pressure sensor 20 may vary. For example, pressure sensor 20 may include a semiconductor (e.g., silicon wafer) pressure sensor, piezoelectric pressure sensor, a fiber optic or optical pressure sensor, a Fabry-Perot type pressure sensor, an ultrasound transducer and/or ultrasound pressure sensor, a magnetic pressure sensor, a solid-state pressure sensor, or the like, or any other suitable pressure sensor.

As indicated above, pressure sensor 20 may include an optical pressure sensor. In at least some of these embodiments, an optical fiber 24 may be attached to pressure sensor 20 and may extend proximally therefrom. An attachment member 26 may attach optical fiber 24 to shaft 12. Attachment member 26 may be circumferentially disposed about and attached to optical fiber 24 and may be secured to the inner surface of shaft 12 (e.g., distal portion 16). In at least some embodiments, attachment member 26 is proximally spaced from pressure sensor 20. Other arrangements are contemplated. In some instances, a centering ring (not shown) may be disposed around optical fiber 24 at a position that is spaced proximally from optical pressure sensor 20.

In at least some embodiments, distal portion 16 may include a region with a thinned wall and/or an increased inner diameter that defines a housing region 52. In general, housing region 52 is the region of distal portion 16 that ultimately "houses" the pressure sensor (e.g., pressure sensor 20). By virtue of having a portion of the inner wall of shaft 12 being removed at housing region 52, additional space may be created or otherwise defined that can accommodate sensor 20.

In at least some embodiments, it may be desirable for pressure sensor 20 to have reduced exposure along its side surfaces to fluid pressure (e.g., from the blood). Accordingly, it may be desirable to position pressure sensor 20 adjacent a landing region 50 defined along housing region 52. Landing region 50 may be substantially free of slots 18 so that the side surfaces of pressure sensor 20 have a reduced likelihood of being deformed due to fluid pressures at these locations. Distal of landing area 50, housing region 52 may include slots 18 that provide fluid access to pressure sensor 20. Slots 18 (e.g., slots 18 positioned distally of landing area 50) may define a fluid pathway that allows blood (and/or a body fluid) to flow from a position along the exterior or outer surface of guidewire 10 (and/or shaft 12), through slots 18, and into the lumen 22 of shaft 12 where the blood can come into contact with pressure sensor 20. Because of this, no additional side openings/holes (e.g., other than slots 18) may be necessary in shaft 12 for pressure measurement. This may also allow the length of distal portion 16 to be shorter than typical sensor mounts or hypotubes that would need to have a length sufficient for a suitable opening/hole (e.g., a suitable "large" opening/hole) to be formed therein that provides fluid access to sensor 20. In some instances, one, two, three, four, or more slots (e.g., round slots, oval slots, elongated slots, etc.), different from slots 18, may be formed in housing region 50 adjacent to or just distal of pressure sensor 20 that are intended to be a fluid pathway for blood to come into contact with pressure sensor 20.

A tip member 30 may be coupled to distal portion 16. Tip member 30 may include a shaping member 32 and a spring or coil member 34. A distal tip 36 may be attached to shaping member 32 and/or spring 34. In at least some embodiments, distal tip 36 may take the form of a solder ball tip. Tip member 30 may be joined to distal portion 16 of shaft 12 with a bonding member 46 such as a weld.

Shaft 12 may include a hydrophilic coating 19. In some embodiments, hydrophilic coating 19 may extend along substantially the full length of shaft 12. In other embodiments, one or more discrete sections of shaft 12 may include hydrophilic coating 19.

Figure 2:
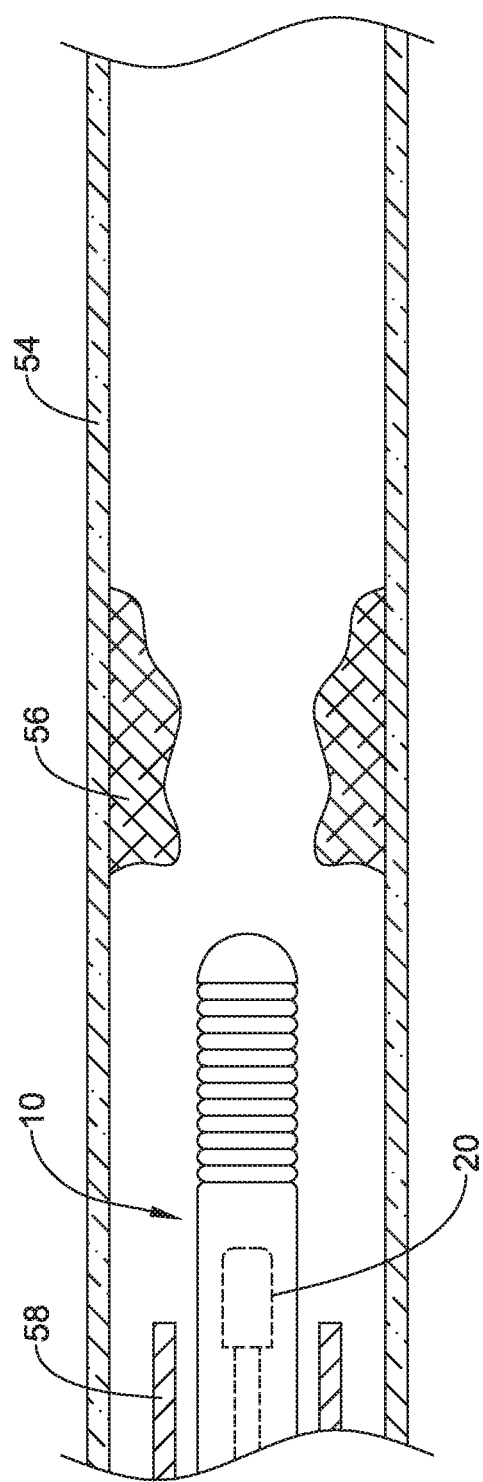
FIG. 2 is a side view of an example medical device disposed in a blood vessel.
Figure 3:
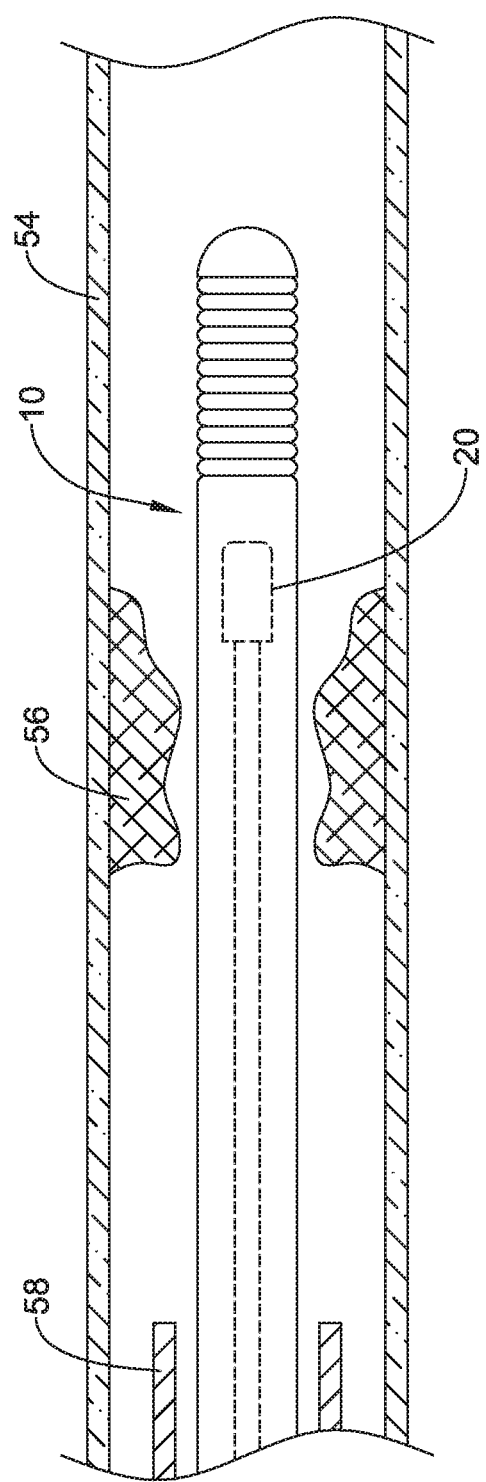
FIG. 3 is a side view of an example medical device disposed in a blood vessel.

In use, a clinician may use guidewire 10 to measure and/or calculate FFR (e.g., the pressure after an intravascular occlusion relative to the pressure before the occlusion and/or the aortic pressure). Measuring and/or calculating FFR may include measuring the aortic pressure in a patient. This may include advancing guidewire 10 through a blood vessel or body lumen 54 to a position that is proximal or upstream of an occlusion 56 as shown in FIG. 2. For example, guidewire 10 may be advanced through a guide catheter 58 to a position where at least a portion of sensor 20 is disposed distal of the distal end of guide catheter 58 and measuring the pressure within body lumen 54. This pressure may be characterized as an initial pressure. In some of these and in other embodiments, the aortic pressure may be measured by another device (e.g., a pressure sensing guidewire, catheter, or the like). The initial pressure may be equalized with the aortic pressure. For example, the initial pressure measured by guidewire 10 may be set to be the same as the measured aortic pressure. Guidewire 10 may be further advanced to a position distal or downstream of occlusion 56 as shown in FIG. 3 and the pressure within body lumen 54 may be measured. This pressure may be characterized as the downstream or distal pressure. The distal pressure and the aortic pressure may be used to calculate FFR. It can be appreciated that an FFR system that utilizes an optical pressure sensor in a pressure sensing guidewire may be connected to a number of processing/conditioning units, displays, and the like. When making these connections, the various cables/connections may be designed so that the optical signals can be transmitted between adjacent optical fibers in an efficient manner.

In a number of instances, multiple lesions may be present within a blood vessel. Treatment of multiple lesions may include placing a pressure sensing guidewire (e.g., guidewire 10) distal of the lesion and then proximally retracting the pressure sensing guidewire to a position that is proximal of the lesions (e.g., all the lesions). This may be a continuous proximal retraction of the pressure sensing guidewire while simultaneously taking pressure measurements. After these initial pressure measurements, a clinician may decide treat one of the lesions, for example by deploying a stent, if the FFR value is below a clinically relevant threshold (e.g., about 0.75 to 0.80 or less). The process may then be repeated, sometimes multiple times, with several lesions being treated with a stent until a satisfactory outcome (e.g., where the FFR value is increased to about 0.75 to 0.80 or more) is achieved. The repeated pressure measurements and repeated treatment steps may extend the amount of time it takes to treat the patient. Furthermore, the repeated processes may result in the deployment of more stents than may be necessary in order to achieve a clinically satisfactory increase in flow. Because of this, it may be desirable to shorten the amount of time for a clinical procedure, deploy as few stents as possible, and select the lesion(s) that provide the greatest improvement for the patient. Disclosed herein are methods for estimating the FFR along a multi-lesion vascular region based that would result upon the treatment of different combinations of the lesions after a percutaneous coronary intervention (PCI). The methods utilize a computational approach to assess/predict/estimate post-PCI FFR so that a clinician can select a desirable treatment regime for a patient that has a high likelihood of success, reduces the overall procedure time, allows for an appropriate number (e.g., fewer) of stents to be deployed, etc.

Figure 4:
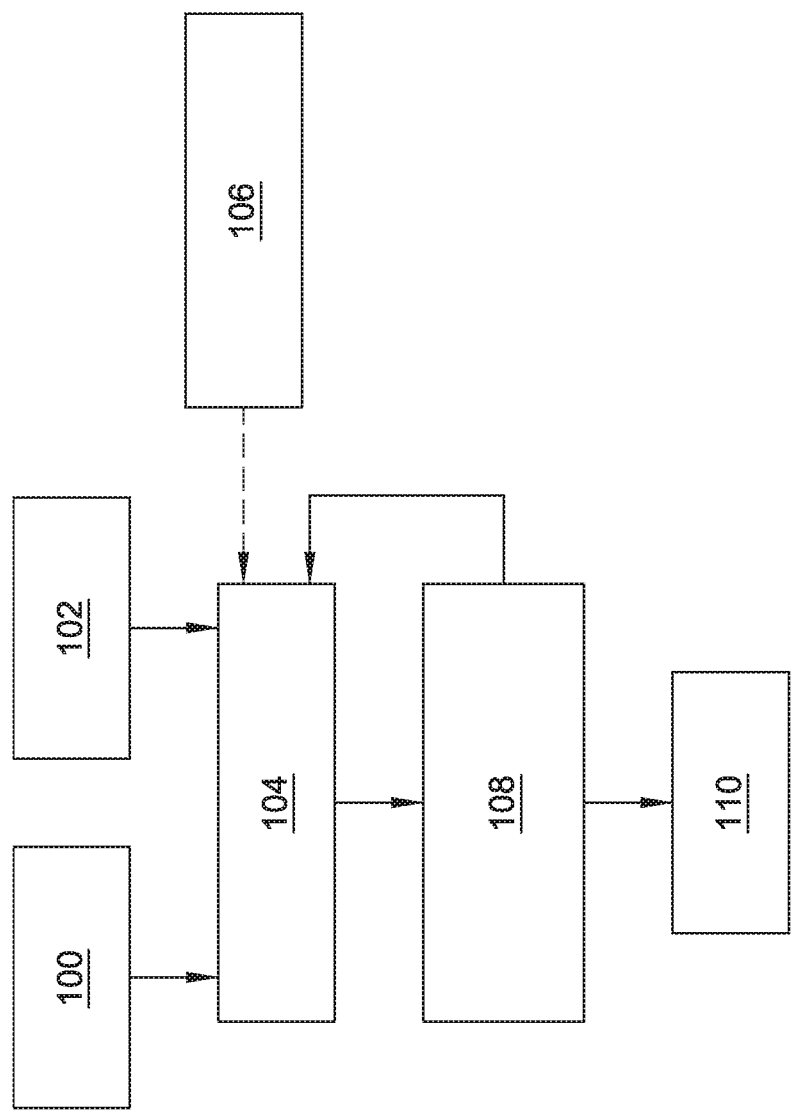
FIG. 4 is a flow chart depicting an example method.

A flow chart depicting at least some of the methods contemplated is provided at FIG. 4. In box 100, pressure measurements prior to PCI and/or pre-PCI FFR measurements are taken. This may include taking pressure measurements with guidewire 10, a pressure sensing catheter, and/or a pressure sensing medical device. At box 102, imaging data (e.g., for co-registering) may also be collected. This may include the use of intravascular ultrasound. At box 104, the estimated post-PCI FFR may be calculated as disclosed herein. In some instances, this may optionally include taking into consideration the gradient of collateral flow, which may be input by a physician at box 106. At box 108, the physician may evaluate the calculations and choose a stenting strategy. Finally, at box 110, an optimized stenting strategy may be implemented.

Generally, the computational approach for estimating post-PCI FFR values may be determined using the following equation (equation 1):

$$FFR_{post} = \frac{P_d}{P_a - \int P_g} \quad (1)$$

where $FFR_{post}$ is the estimated post-PCI FFR for a given treatment, $P_a$ is the aortic pressure (e.g., as measured upstream of the lesion(s) or via another devices such as a catheter positioned within the aorta), $P_d$ is the distal pressure (e.g., the pressure distal of the lesion(s)), and $P_g$ is the pressure gradient across the lesion(s).

The post-PCI estimation for FFR for a single lesion may be also determined using the following equation (equation 2) and the result of value is same as equation 1:

$$FFR_{m\_post}=P_d/(P_a-(P_{mp}-P_{md})) \quad (2)$$

where $FFR_{m\_post}$ is the estimated post-PCI FFR, $P_a$ is the aortic pressure, $P_d$ is the distal pressure, $P_{mp}$ is the pressure proximal of the lesion, and $P_{md}$ is the pressure distal of the lesion. Either equation 1 and equation 2, depending on the situation, can be utilized to calculate an estimated post-PCI FFR value. Based on the estimated post-PCI FFR value, a clinician may decide if a particular treatment option (or any one or more of available treatment options) are suitable for treating the patient.

Figure 5:
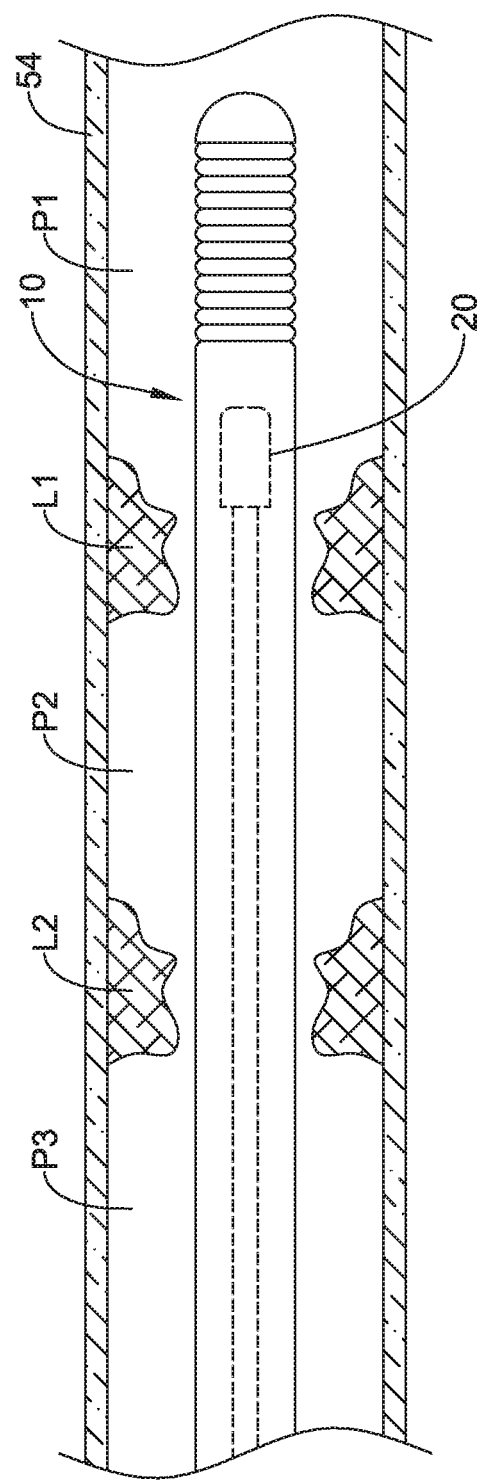
FIG. 5 is a side view of an example medical device disposed in a blood vessel.

FIGS. 5-8 illustrate an example application of using an estimated post-PCR FFR computation for selecting a treatment for a patient. FIG. 5 schematically illustrates guidewire 10 disposed in blood vessel 54. It can be appreciated that in other instances another pressure sensing medical device may be utilized. In this example, blood vessel 54 includes two lesions, namely a first lesion L1 and a second lesion L2 disposed proximal of first lesion L1. Pressure measurements can be taken at various positions within blood vessel 54. For example, pressure measurements can be taken with guidewire 10 at a first position P1 distal of first lesion L1, at a second position P2 proximal of first lesion L1 and distal of second lesion L2, and at a third position P3 proximal of second lesion L2. In at least some instances, the pressure measurements can be taken while continuously pulling back guidewire 10. The pressure measurements at first position P1, second position P2, and at third position P3 can be used to determine FFR at each of the positions P1 and P2. In at least some instances, the FFR at third position P3 may be assumed to be approximately 1.0 or may be approximately 1.0.

Figure 6:
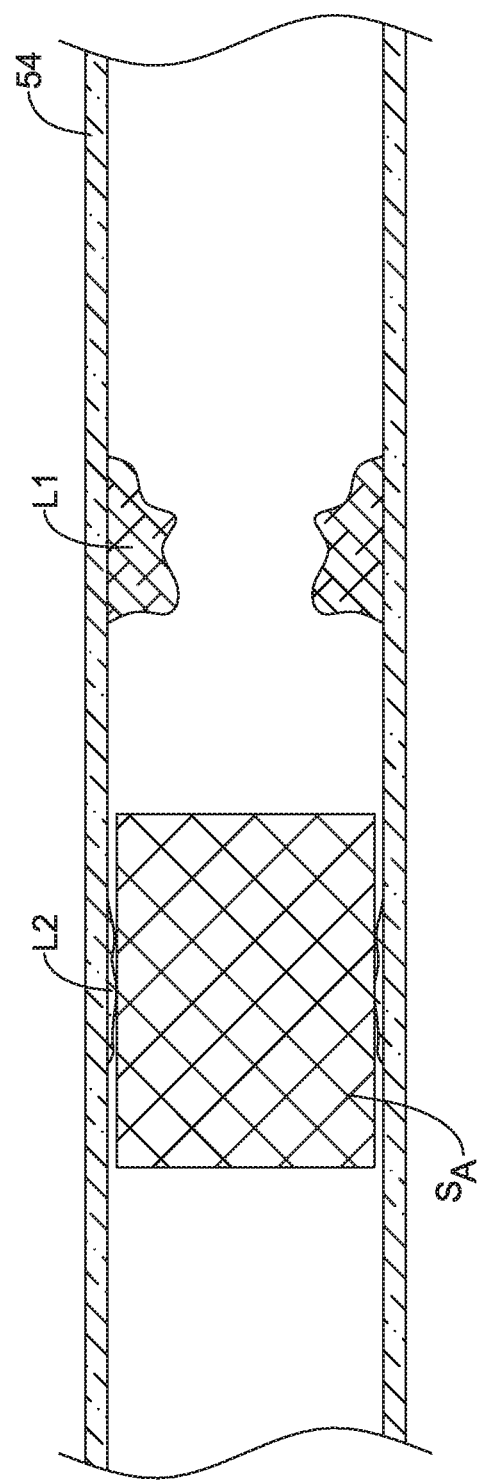
FIG. 6 schematically illustrates a treatment strategy for treating one or more intravascular lesions.
Figure 7:
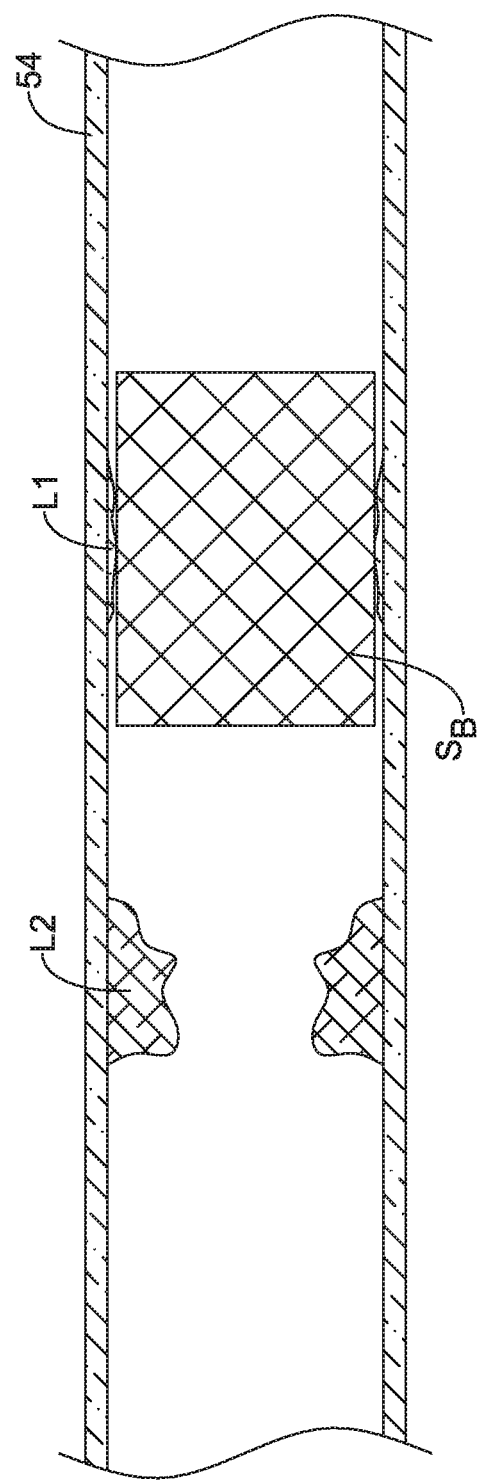
FIG. 7 schematically illustrates a treatment strategy for treating one or more intravascular lesions.
Figure 8:
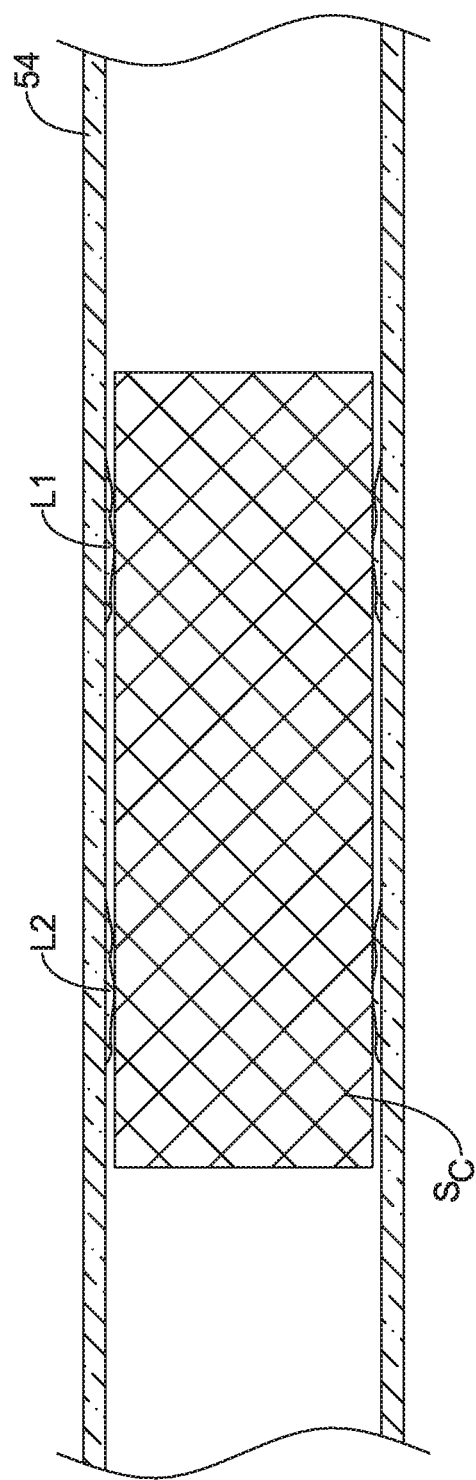
FIG. 8 schematically illustrates a treatment strategy for treating one or more intravascular lesions.

A clinician may have a number of different treatment options for treating first lesion L1 and/or second lesion L2. For example, the clinician may decide to deploy a stent $S_A$ across second lesion L2 as schematically illustrated in FIG. 6, deploy a stent $S_B$ across first lesion L1 as schematically illustrated in FIG. 7, or deploy a stent $S_C$ across both first lesion L1 and second lesion L2 as schematically depicted in FIG. 8. In cases where the severity of first lesion L1 and the severity of second lesion L2 is similar (e.g., there is a similar pressure gradient across both first lesion L1 and second lesion L2), treatment of just one of the lesion may be sufficient achieve a satisfactory clinical outcome. Alternatively, treatment of both lesions L1, L2 may be necessary in order to achieve a satisfactory result.

In order to determine the most desired treatment option, a post-PCI FFR value estimation may be calculated, for example, using equation 1. When doing so, the estimated post-PCI FFR values for treating only first lesion L1, only second lesion L2, or both first lesion L1 and second lesion L2 can be determined and the clinician can select a desirable treatment option based on these calculations. The calculations may be performed using a processing unit and/or interferometer that is programmed with software for making the calculations. In some instances, the results of the calculations can be output to a display unit. The results may be displayed as estimated post-PCI FFR values or more schematically using graphics to represent the possible treatment options and the estimated post-PCI FFR value for each of the treatment options. Other processing, calculation, and display options are contemplated.

In some instances, an imaging device (not shown) may be utilized to determine the position of guidewire 10 during the pressure measurements. For example, the imaging device may be used to co-register the location of guidewire 10 with other data (e.g., location data) such as fluoroscopic image data of the vasculature so that, for example, the location at which the pressure measurements are made can be more accurately co-registered with the location of lesions within the vasculature. In some instances, the imaging device may include an ultrasound imaging device such as an intravascular ultrasound (IVUS) device. Other imaging devices are contemplated including an X-ray imaging device, an angiographic imaging device, an optical coherence tomography imaging device, a computerized tomography imaging device, or the like.

In some instances, the imaging system can be used to perform "virtual stenting" or "automatic lesion assessment". For example, guidewire 10 (and/or another pressure sensing medical device) can be utilized to measure pressure (and/or determine FFR) along the length of a vessel and the pressure can be registered with image of the vessel. A virtual stent or stents can be placed along the vessel on the display of the registered pressure and image data and the post-PCI FFR value can be estimated (and, in at least some instances, the post-PCI FFR value can be displayed). It may be possible to toggle between a variety of different stenting strategies so that the clinician can visualize and assess the benefits of different stenting strategies and, ultimately, choose a desired stenting strategy.

Figure 9:
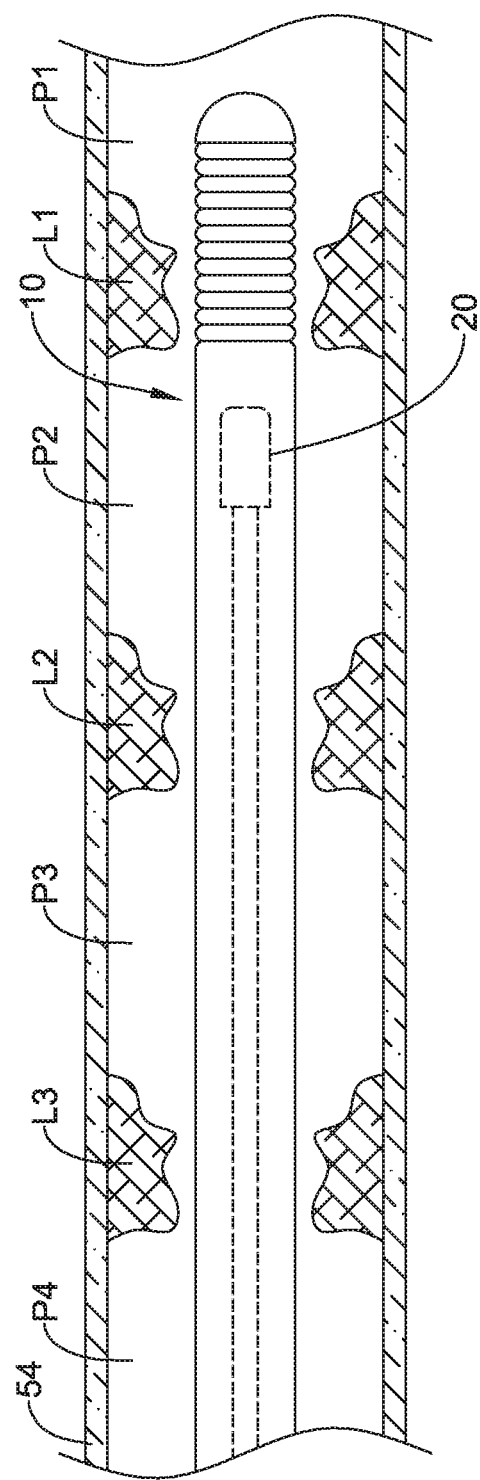
FIG. 9 is a side view of an example medical device disposed in a blood vessel.

FIG. 9 schematically illustrates guidewire 10 disposed in blood vessel 54. It can be appreciated that in other instances another pressure sensing medical device may be utilized. In this example, blood vessel 54 includes three lesions, namely a first lesion L1, a second lesion L2 disposed proximal of first lesion L1, and a third lesion L3 disposed proximal of second lesion L2. Pressure measurements can be taken at various positions within blood vessel 54. For example, pressure measurements can be taken using guidewire 10 at a first position P1 distal of first lesion L1, at a second position P2 proximal of first lesion L1 and distal of second lesion L2, at a third position P3 proximal of second lesion L2 and distal of third lesion L3, and at a fourth position P4 proximal of third lesion L3. In at least some instances, the pressure measurements can be taken while continuously pulling back guidewire 10. These pressure measurements can be used to determine FFR at each of the positions P1, P2, and P3. In at least some instances, the FFR at fourth position P4 may be assumed to be approximately 1.0 or may be approximately 1.0.

Figure 10:
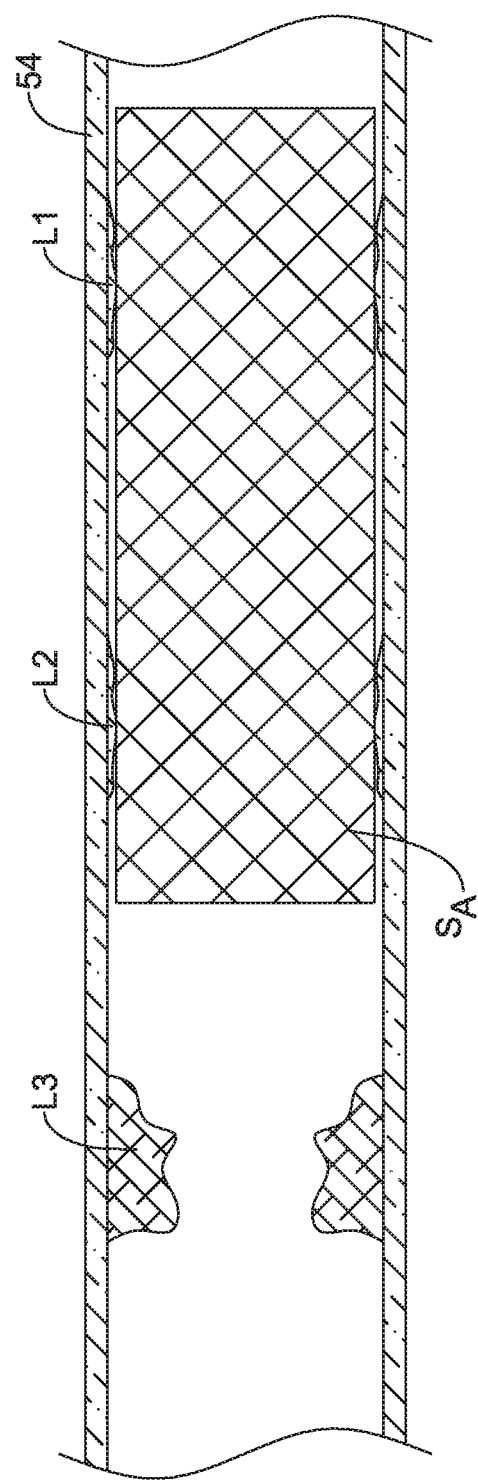
FIG. 10 schematically illustrates a treatment strategy for treating one or more intravascular lesions.
Figure 11:
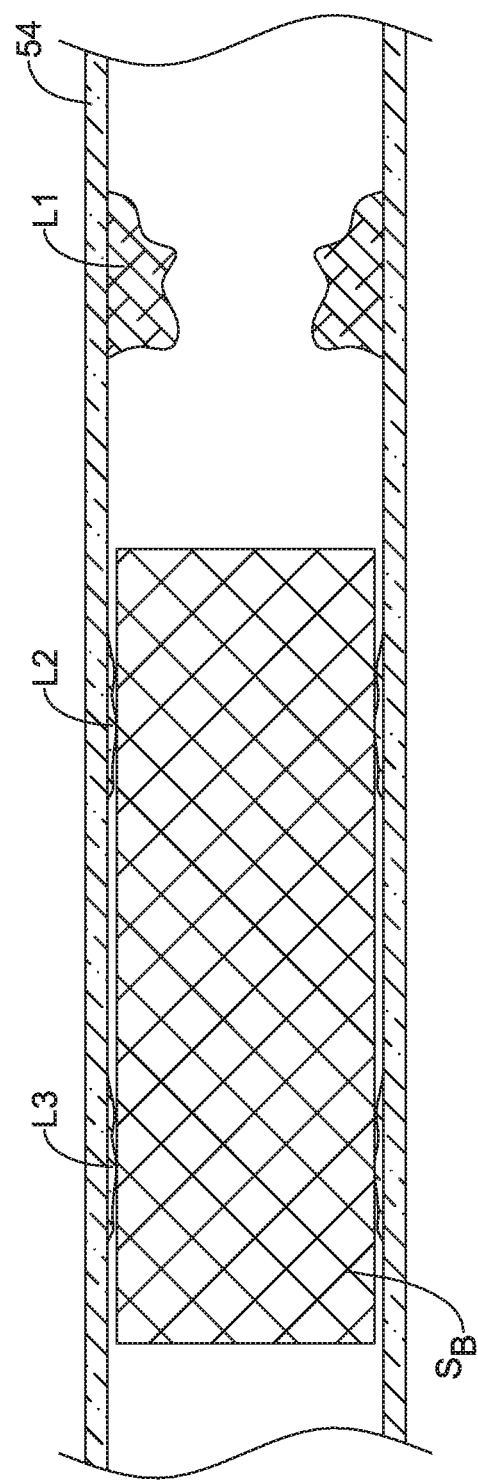
FIG. 11 schematically illustrates a treatment strategy for treating one or more intravascular lesions.
Figure 12:
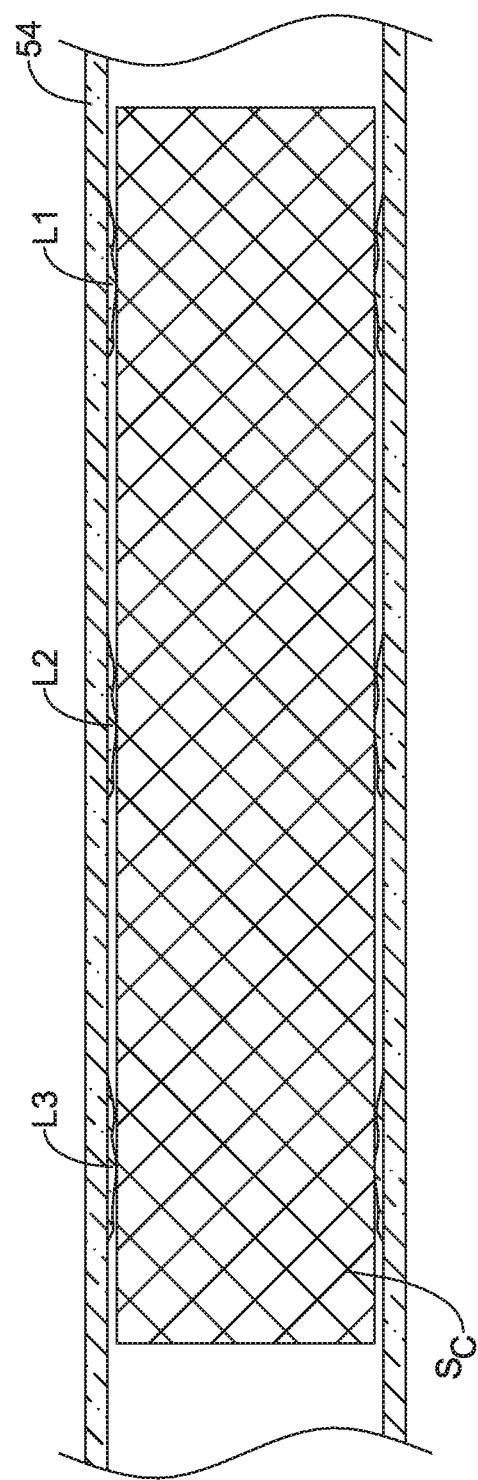
FIG. 12 schematically illustrates a treatment strategy for treating one or more intravascular lesions.

A clinician may have a number of different treatment options for treating first lesion L1, second lesion L2, third lesion L3, or combinations thereof. For example, the clinician may decide to deploy a stent $S_A$ across first lesion L1 and second lesion L2 (without treating third lesion L3) as schematically illustrated in FIG. 10, deploy a stent $S_B$ across second lesion L2 and third lesion L3 (without treating first lesion L1) as schematically illustrated in FIG. 11, or deploy a stent $S_C$ across all three lesions L1, L2, and L3 as schematically depicted in FIG. 12. Other treatment options may also be considered including the treatment of only first lesion L1, treatment of only second lesion L2, treatment of only third lesion L3, and treatment of first lesion L1 and third lesion L3 (without treating second lesion L2).

In order to determine the most desired treatment option, a post-PCI FFR value estimation may be calculated, for example, using equation 1. When doing so, the estimated post-PCI FFR values for treating, for example, first lesion L1 and second lesion L2 (without treating third lesion L3), second lesion L2 and third lesion L3 (without treating first lesion L1), or all three lesions L1, L2, and L3 can be determined and the clinician can select a desirable treatment option based on this calculation. As indicated above, the calculations may be performed using a processing unit and/or interferometer that is programmed with software for making the calculations. In some instances, the results of the calculations can be output to a display unit. The results may be displayed as estimated post-PCI FFR values or more schematically using graphics to represent the possible treatment options and the estimated post-PCI FFR value for each of the treatment options. Other processing, calculation, and display options are contemplated.

In some instances, an imaging device (not shown) may be utilized to determine the position of guidewire 10 during the pressure measurements. For example, the imaging device may be used to co-register the location of guidewire 10 with other data (e.g., location data) such as fluoroscopic image data of the vasculature so that, for example, the location at which the pressure measurements are made can be more accurately co-registered with the location of lesions within the vasculature. In some instances, the imaging device may include an ultrasound imaging device such as an intravascular ultrasound (IVUS) device. Other imaging devices are contemplated including an X-ray imaging device, an angiographic imaging device, an optical coherence tomography imaging device, a computerized tomography imaging device, or the like.

For illustration purposes, some example calculations of the estimated post-PCI FFR values for (a) treating first lesion L1 and second lesion L2 (without treating third lesion L3) or (b) treating second lesion L2 and third lesion L3 (without treating third lesion L1) are provided for the multi-lesion intravascular region illustrated in FIGS. 9-12. If collateral flow is small and can be ignored for FFR, the calculations may utilize equation 1.

$$FFR_{post} = \frac{P_d}{P_a - \int P_g} \quad (1)$$

Using equation 1 to determine $FFR_{post}$ for treatment option (a) may include plugging in the actual pressure measurements at the appropriate positions. For example, $P_d$ equates to the pressure at first position P1. $P_a$ equates to the aortic pressure (e.g., which may approximate the pressure at fourth position P4). The integral of the pressure gradient equates to the pressure drop across the stenting zone (e.g., the pressure at third position P3 minus the pressure at first position P1).

In some instances, equation 1 can be modified to simplify the calculation for treatment option (a). For example, if $P_d$ is divided by $P_a$, the result is $P_d/P_a$, which equates to the FFR value at first position P1 ($FFR_1$) and P1 is the distal portion of vessel. If $(P_a - (\int P_g))$ is also divided by $P_a$, the result is 1−(the difference between the FFR value at position P3, $FFR_3$, and the FFR value at position P1, $FFR_1$). Thus, the following equation (equation 3) can be used to estimate the post-PCI FFR value ($FFR_{post}$) resulting from treatment option (a):

$$FFR_{post} = FFR_1/(1-(FFR_3-FFR_1)). \quad (3)$$

For example, if $FFR_1$ is determined to be 0.68 and $FFR_3$ is determined to be 0.90, $FFR_{post}$ would be calculated as 0.872. The estimated FFR value for this treatment option would result in a clinically satisfactory outcome.

Using equation 1 to determine $FFR_{post}$ for treatment option (b) may include plugging in the actual pressure measurements at the appropriate positions. For example, $P_d$ equates to the pressure at second position P2. $P_a$ equates to the aortic pressure (e.g., which may approximate the pressure at fourth position P4). The integral of the pressure gradient equates to the pressure drop across the stenting zone (e.g., the pressure at fourth position P4 minus the pressure at second position P2).

In a manner similar to what is described above in relation to treatment option (a), equation 1 can be modified to simplify the calculation for treatment option (b). For example, if $P_d$ is divided by $P_a$, the result is $P_d/P_a$, which equates to the FFR value at first position P1 ($FFR_1$). If $(P_a - (\int P_g))$ is also divided by $P_a$, the result is 1−(the difference between the FFR value at position P4, $FFR_4$, and the FFR value at position P2, $FFR_2$). Thus, the following equation (equation 4) can be used to estimate the post-PCI FFR value ($FFR_{post}$) resulting from treatment option (b):

$$FFR_{post} = FFR_1/(1-(FFR_4-FFR_2)). \quad (4)$$

Because $FFR_4$ may be the FFR value at a position where there is no lesion, $FFR_4$ may be set at 1.0. Therefore, equation 4 can be further modified into equation 5:

$$FFR_{post} = FFR_1/(1-(1-FFR_2)). \quad (5)$$

If $FFR_1$ is determined to be 0.68 and $FFR_2$ is determined to be 0.82, $FFR_{post}$ would be calculated as 0.819. The estimated FFR value for this treatment option would result in a clinically satisfactory outcome.

Based on these example calculations, either treatment option (a) or treatment option (b) would be likely to result in a clinically beneficial outcome. Because the clinician would have confidence that either treatment option would result in a favorable outcome, other factors can be considered. For example, treating lesions that are more "upstream", such as third lesion L3, may increase flow to a larger number of downstream areas. Thus, a clinician may favor treating more upstream lesions when there is a high level of confidence that treating the upstream lesions would suitable increase the FFR valve.

In at least some instances, the post-PCI FFR may be predicted without taking into account collateral flow. For example, it has been observed that in most instances, collateral flow would add a relatively small amount of uncertainty (e.g., about 10% or less) in the post-PCI FFR calculation. However, it may be useful to also take into account collateral flow, for example, by monitoring the gradient of collateral flow. When doing so, equation 1 may be modified as follows:

$$\frac{FFRpost-coll}{FFRpost} = \frac{(FFR_{before\ PCI} - A)(1-B)}{(1-B-A)FFR_{before\ PCI}} + A \cdot \frac{1-B-FFR_{before\ PCI}}{1-B-A} \cdot \frac{1-B}{FFR_{before\ PCI}} \quad \text{equation 1-C}$$

where $FFR_{post-coll}$ is the estimated post-PCI FFR taking into account collateral flow, $FFR_{post}$ is the post-PCI FFR without taking into account collateral flow, $P_a$ is the aortic pressure, $P_d$ is the distal pressure, $P_w$ is the coronary wedge pressure, and $\Delta P$ is the pressure gradient across the stenting zone, $$FFR_{before\ PCI} = \frac{Pd}{Pa}, A = \frac{Pw}{Pa} \text{ and } B = \frac{\Delta PG}{Pa}.$$

This equation allows for the calculation of the estimated post-PCI FFR taking into account the grade of collateral flow. As indicated above, in at least some, if not most, clinical settings the collateral flow has a relatively small impact on the estimated post-PCI FFR calculations (e.g., when the coronary wedge pressure approaches 0, the result of equation 1-C approximates 1). However, because the collateral flow may be measured during an intervention, it may be beneficial to calculate the estimated post-PCI FFR while taking into account the collateral flow in order to ensure the most accurate calculations.

EXAMPLE

To determine the impact of collateral flow on the estimated post-PCI FFR values, the ratio of $FFR_{post-coll}$:$FFR_{post}$ is calculated by equation 1-C was estimated in various situations. The ratio ranged from 0 to 0.4, and the measured FFR before PCI ranged from 0.6 to 1.0. It is believed that these values are representative of most cases. $\Delta PG/P_a$ may be limited between 0 to 0.4 because FFR before PCI range from 0.6 to 1.0. As the result, the ratio of $FFR_{post-coll}$:$FFR_{post}$ is in between 0.9 and 1.0. The ratio of $FFR_{post-coll}$:$FFR_{post}$ inversely correlates with $P_w/P_a$ and positively correlates with FFR before PCI. On the other hand this ratio changes for $\Delta PG/P_a$ with an inflection point like quadric curve. $P_w$ may not exceed 30 mmHg in the cases without visible collaterals as a $P_w > 30$ mm Hg may be an indicator for collaterals. This suggests that $P_w/P_a$ may not exceed 0.2 to 0.3 in cases without visible collaterals. The ratio of $FFR_{post-coll}$:$FFR_{post}$ ranges 0.90 to 1.0 and, thus, FFR after PCI can be predicted without Pw with an uncertainty of <10% in clinical settings.

Secondly, the ratio of $FFR_{post-coll}$:$FFR_{post}$ was estimated under typical conditions and FFR measurements were taken. Mean FFR before PCI was 0.71 and mean $\Delta P/P_a$ was 0.15 in our cases. The ratio of $FFR_{post-coll}$:$FFR_{post}$ inversely correlates with $P_w/P_a$, however the ratio ranged from 0.9 to 1.0 below $P_w/P_a$ 0.65. A value for $P_w/P_a = 0.65$ indicates that the coronary artery was near chronic total occlusions.

Finally, the ratio of $FFR_{post-coll}$:$FFR_{post}$ was plotted for essentially all kinds of conditions. Nine diagrams were formed and each FFR value ranged from 0.1 to 0.9. The relationship between the ratio of $FFR_{post-coll}$:$FFR_{post}$ were plotted, changing the $P_w/P_a$ every 0.05 or 0.1. in each diagram. The predicted value with equation 1-C is a little larger than the result with our equation 1. $P_w/P_a$ do not exceed FFR pre PCI and $\Delta PG/Pa$ do not exceed 1-FFR. $P_w/P_a$=FFR pre PCI means the coronary artery was completely occluded totally and $\Delta PG/P_a=(1-FFR)$ means that no stenosis existed other than stenting site.

What is claimed is:

1. A method for diagnosing and/or treating an intravascular region, the method comprising the steps of:
    advancing a pressure sensing device through an ostium of a vessel to a first position beyond a first lesion;
    retracting the pressure sensing device to a second position just before the pressure sensing device reaches the first lesion;
    retracting the pressure sensing device further to a third position just after the pressure sensing device passes the first lesion;
    retracting the pressure sensing device further to a fourth position near the ostium of the vessel;
    calculating a first estimated post-treatment fractional flow reserve based on treatment of the first lesion;
    treating the first lesion based on the first estimated post-treatment fractional flow reserve,
    wherein said step of calculating the first estimated post-treatment fractional flow reserve includes:
        measuring a distal pressure ($P_d$) at the first position,
        measuring a distal pressure of the first lesion ($P_{md}$) at the second position,
        measuring a proximal pressure of the first lesion ($P_{mp}$) at the third position, and
        measuring an aortic pressure ($P_a$) at the fourth position so that the first post-treatment estimated fractional flow reserve is calculated to be equal to:

$$P_d/(P_a-(P_{mp}-P_{md})).$$

2. The method of claim 1, wherein said step of calculating the first estimated post-treatment fractional flow reserve includes:
    determining a first fractional flow reserve ($FFR_1$) at the first position, and
    determining a second fractional flow reserve ($FFR_2$) at the second position; and
    determining a third fractional flow reserve ($FFR_3$) at the third position; and
    so that a third estimated fractional flow reserve is equal to:

$$FFR_1/(1-(FFR_3-FFR_2)).$$

3. The method of claim 2, further comprising the step of calculating a third estimated post-treatment fractional flow reserve based on the first estimated post-treatment fractional flow reserve.

4. The method of claim 1, further comprising the step of co-registering a location of the pressure sensing device relative to the first lesion with an imaging device.

5. The method of claim 1, wherein said step of calculating the first estimated post-treatment fractional flow reserve is based on images from an imaging device including an ultrasound imaging device, an X-ray imaging device, an angiographic imaging device, an optical coherence tomography imaging device, or a computerized tomography imaging device.

6. The method of claim 1, wherein said step of treating the first lesion based on the first estimated post-treatment fractional flow reserve includes grade of collateral flow adjacent to the first lesion.

7. A method for diagnosing and/or treating a medical condition, the method comprising the steps of:
    advancing a pressure sensing guidewire through an ostium of a vessel to a first position beyond a plurality of lesions, the pressure sensing guidewire comprising:
        an elongate shaft having a distal housing region,
        an optical pressure sensor disposed within the distal housing region, and
        an optical fiber coupled to the optical pressure sensor and extending proximally therefrom;
    retracting the pressure sensing guidewire over the lesions;
    retracting the pressure sensing guidewire to a second position near the ostium of the vessel;
    calculating an estimated fractional flow reserve value; and
    treating at least one of the lesions based on the estimated fractional flow reserve value, wherein said step of calculating the estimated fractional flow reserve value includes:

measuring a distal pressure distal ($P_d$) at the first position, measuring an aortic pressure ($P_a$) at the second position, measuring a pressure gradient ($P_g$) across at least two of the lesions so that the estimated fractional flow reserve is calculated to be equal to:

$$P_d/(P_a-(fPg)).$$

8. The method of claim 7, further comprising the step of co-registering a location of the pressure sensing guidewire with an imaging device.

9. The method of claim 7, wherein said lesions includes a first lesion, a second lesion disposed proximal of the first lesion, and a third lesion disposed proximal of the second lesion.

* * * * *